Figure 1:
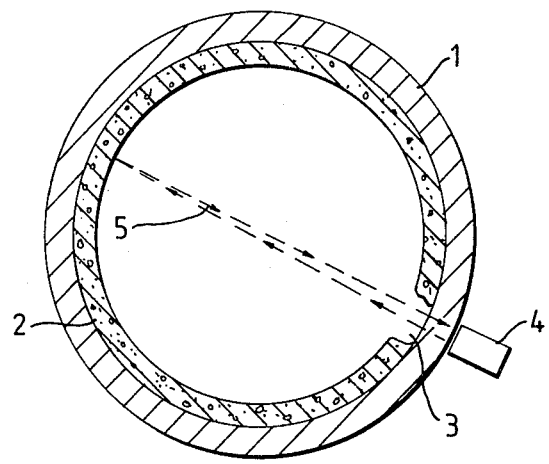

United States Patent [19]

Jackson

[11] 4,446,736
[45] May 8, 1984

[54] ULTRASONIC IDENTIFICATION OF DAMAGE IN LINED STRUCTURES

[75] Inventor: Peter Jackson, Stockton-On-Tees, England

[73] Assignee: Imperial Chemical Industries PLC, London, England

[21] Appl. No.: 305,354

[22] Filed: Sep. 24, 1981

[30] Foreign Application Priority Data

Oct. 10, 1980 [GB] United Kingdom ................ 8032874

[51] Int. Cl.³ ............................................ G01N 29/04
[52] U.S. Cl. ......................................... 73/600; 73/629
[58] Field of Search ................ 73/600, 620, 622, 627, 73/629, 599, 628, 609

[56] References Cited

U.S. PATENT DOCUMENTS

| | | | |
|---|---|---|---|
| 3,036,151 | 5/1962 | Mitchell et al. ...................... | 73/620 |
| 3,308,651 | 3/1967 | Cullen .................................. | 73/600 |
| 3,777,552 | 12/1973 | Fletcher . | |
| 3,813,926 | 6/1974 | Stubbeman ............................ | 73/609 |
| 3,940,952 | 3/1976 | Mitchell ................................ | 73/629 |
| 4,187,425 | 2/1980 | Thompson ........................ | 250/358 P |

FOREIGN PATENT DOCUMENTS

1207730 12/1965 Fed. Rep. of Germany .
316005 11/1971 U.S.S.R. ................................ 73/622

OTHER PUBLICATIONS

J. Krautkramer et al., "Werkstoffprufung mit Ultraschall", 3rd Edition 1975, Springer Verlag, Berlin, Heidelberg, New York, p. 515.

*Primary Examiner*—James J. Gill
*Attorney, Agent, or Firm*—Cushman, Darby & Cushman

[57] ABSTRACT

A method of testing the integrity of the internal lining of a hollow body, especially a pipeline, by transmitting an ultrasonic wave from the exterior of the body through the adjacent wall of the body and monitoring the wave, if any, reflected from the opposite wall. In many cases, especially concrete linings, an intact or partially intact lining on the adjacent wall will absorb the ultrasonic wave and there is no reflected wave. A reflected wave frequently indicates loss of the lining on the adjacent wall although in some cases depending on, for example, the thickness of the lining or the material of which it is made, a reflected wave may be obtained even when the lining is intact. In such cases comparison of the reflected wave with predetermined standards provides an indication of whether or not the lining is intact.

2 Claims, 2 Drawing Figures

ULTRASONIC IDENTIFICATION OF DAMAGE IN LINED STRUCTURES

The present invention relates to a method for identifying damage in lined structures, for example lined pipes, using ultrasonics.

The present invention has a particular applicability to the identification of damage to the inner lining of lined pipes and conduits and is described hereinafter with particular reference to that use but it is to be understood that the invention may also be applied to the determination of damage to the inner linings of other hollow bodies, for example storage vessels.

Pipes and conduits are employed in many areas of industry and efficient monitoring of their condition is essential. Many pipes are made of metal and, depending on the metal used and on the material flowing through the pipe, will be subject to a lesser or greater degree to corrosion. Many methods have been proposed which enable the operator to monitor the condition of the pipe and to give warning when it is becoming unsafe to use, for example by measuring the wall thickness of the pipe.

In some cases, the effects of corrosion and/or erosion caused by material flowing through the pipe or conduit are so severe that the pipe or conduit has to be protected with an inner lining so as to give it an acceptable time in service. Several types of material are used for linings including concrete, resin and glass.

Although linings greatly increase the lifetime of pipes and conduits, sooner or later they will begin to deteriorate with age or may even be damaged in use. A need has developed, therefore, for a reliable method of testing the integrity of the lining. In bad cases, a portion of lining may have become completely detached from the inner wall of the pipe, and the pipe is likely then to be very susceptible to corrosion. Methods of detecting incomplete linings have been proposed but for various reasons these methods are difficult to apply. For example, they rely on consistent surface contact between the monitoring apparatus and the exterior of the pipe and such consistent contact cannot always be guaranteed.

We have now surprisingly found that a simple ultrasonic technique enables accurate location to be made of areas where the lining of a pipe or conduit is completely absent.

According to the present invention a method for testing the integrity of the internal lining of a hollow body comprises
(1) transmitting an ultrasonic wave through the wall of the hollow body from the exterior thereof; and
(2) monitoring the reflected wave, if any, which is formed after reflection of the transmitted wave from a point on the internal lining of the wall which is opposite to the point on the wall through which the ultrasonic wave was transmitted.

The hollow body must, of course, contain a fluid, either liquid or gas, which will transmit ultrasonic waves.

The generation of a reflected wave will, in some cases, indicate without any doubt that the internal lining of the wall of the hollow body is non-existent at the point where the transmitted wave passes through the wall. In other cases, the presence of a reflected wave may not be a certain indication that the lining is missing and in these cases it is necessary to compare the reflected wave with a predetermined standard. The distinction between these two sets of cases depends largely on the material of construction of the internal lining and to some extent on the thickness of the lining. For example, if the internal lining is made of concrete, is of a thickness which is usually used in industrial applications and is intact or partially intact the transmitted wave will be totally attenuated by that part of the lining which is attached to the wall at the point where the transmitted wave first enters the wall. No wave will be reflected from the internal lining on the opposite side of the hollow body. On the other hand, if the lining is made of certain other materials, for example resin or glass, there may be cases where the lining, although intact, is not thick enough to attenuate all the transmitted wave. In such cases, a comparison must be made of the reflected wave with a predetermined standard.

Optionally, therefore, the method of the present invention includes the additional step which comprises comparing the magnitude of the reflected wave with a predetermined standard to assess the presence or absence of the lining of the wall at the point where the transmitted wave enters the wall.

The man skilled in the ultrasonics art will have little difficulty in drawing up standards for different lining materials and different thicknesses of lining to enable him to adapt the method of this invention to his own particular needs. As hereinbefore described, for many thicknesses of some materials, for example concrete, it is not necessary to draw up predetermined standards. The mere presence or absence of a reflected wave indicates that the lining is missing or is intact respectively.

The method of the present application may be applied to the identification of damaged linings in lined pipes, conduits, storage vessels, furnaces and the like. A specific example of its use is in monitoring the linings of concrete-lined steel pipes used on oil rigs. At one point, chlorine is injected into the pipeline through a titanium injector. Should any concrete lining be missing then the presence of the titanium injector adjacent to the steel wall will cause electrolytic corrosion and this may be aggravated by the presence of brine and chlorine.

Figure 2:
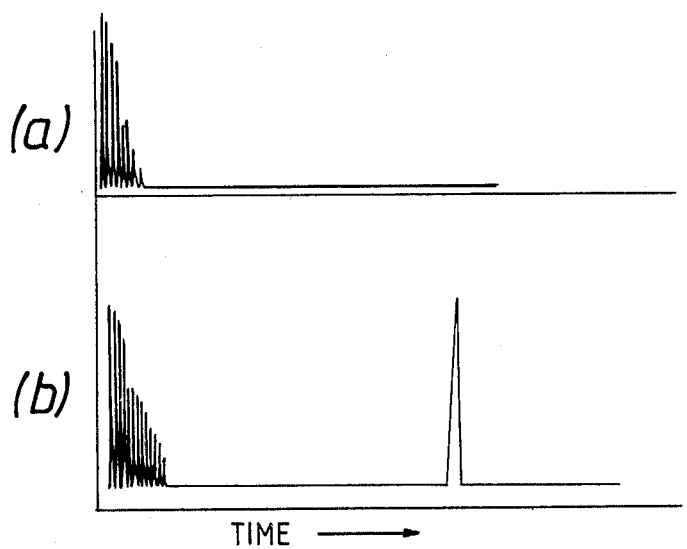

The method of this invention is illustrated further by way of example with reference to the accompanying drawings in which FIG. 1 is a cross-section of a lined pipe and FIG. 2 is an illustration representing reflected beam signals from
(a) a pipe wall with lining intact, and
(b) a pipe wall with damaged lining.

Referring to FIG. 1 of the drawings, a pipe has an outer wall 1 made of steel and an inner lining 2 made of concrete. The lining is shown as having broken away at point 3. A transducer source of ultrasonic waves 4 is shown in position outside the pipe and the path of the ultrasonic waves is shown by the dotted lines 5. The transducer 4 may be moved from point to point around the exterior of wall 1 but for present illustrative purposes it is shown located adjacent the portion of wall 1 having no lining. In use, ultrasonic waves are passed through the wall 1 and the presence or absence of a reflected wave is indicative of the absence or presence respectively of the lining. The transducer 4 is then moved to another position on the wall and the sequence of operations is repeated. Although in this embodiment a single transducer is shown as acting as both source and detector, if desired separate transmitter and detector transducers may be used.

Referring now to FIG. 2, the pattern of reflections of the ultrasonic beam is shown for an undamaged pipe (FIG. 2(a)) and for the damaged pipe of FIG. 1 (FIG. 2(b)). In both FIG. 2(a) and 2(b) the initial heavy trace is caused by reflection from the wall adjacent to transducer 4. FIG. 2(b) also shows a single later trace reflected from the lining opposite to point 3. There is no corresponding trace in FIG. 2(a), the transmitted beam having been completely attenuated by the wall and intact lining.

Thus, whereas some prior art methods can identify areas where the lining is entirely absent only with difficulty, if at all, the method of the present invention will readily identify such areas. At the same time the method of the invention enables potential areas of corrosion to be readily detected before any significant corrosion can occur. The Applicants have also found that the method does not depend for its operation on the source of ultrasonic waves requiring a smooth area of the outer surface of the pipe or other body for its coupling to the pipe. The method also works when the source is located on an irregular area of the pipe's outer surface and this also is a useful advantage over prior art ultrasonic methods where a smooth coupling between the transducer and the surface under investigation is essential. A so-called "couplant" may be used, if desired, to facilitate contact of the transducer source with the surface of the pipe or other body, especially if said surface is irregular in nature. The "couplant" may comprise any liquid medium which transmits ultrasonic waves, for example proprietary greases of various kinds which are known to those skilled in this art or, for example, water squirted across the face of the transducer adjacent the pipe or body surface.

I claim:

1. A method for testing the integrity of an internal lining on the wall of a hollow body at a given location comprising arranging an ultrasonic wave transmitter and an ultrasonic wave receiver exteriorly of the hollow body at said location, generating an ultrasonic wave with the transmitter and transmitting the wave through the wall at said location in a manner such that any transmitted wave which penetrates the wall and the lining, if any, at said location passes through the interior of the hollow body to a point opposite said location and is reflected back toward said location, and detecting any such reflected wave with the receiver at said location, the absence of a reflected wave being an indication of total attenuation by the wall and the lining at said location and hence an indication of the presence of the lining at said location, the presence of a reflected wave being an indication of less than total attenuation by the wall and the lining, if any, at said location and hence an indication of an absence of or a reduced thickness of the lining at said location.

2. A method for testing the integrity of an internal lining on the wall of a hollow body at a given location comprising arranging an ultrasonic wave transmitter and an ultrasonic wave receiver exteriorly of the hollow body at said location, generating an ultrasonic wave with the transmitter and transmitting the wave through the wall at said location in a manner such that any transmitted wave which penetrates the wall and the lining, if any, at said location passes through the interior of the hollow body to a point opposite said location and is reflected back toward said location, and detecting any such reflected wave with the receiver at said location, the ultrasonic wave being selected so that if the liner at said location is intact and undamaged the wave will be totally attenuated by the liner and the wall at said location whereby the absence of wave detection is an indication of an intact and undamaged liner at said location and whereby the presence of wave detection is an indication of the absence of or a reduced thickness of the lining at said location as a result of incomplete attenuation.

* * * * *